United States Patent
Mohan et al.

(10) Patent No.: US 11,773,360 B2
(45) Date of Patent: Oct. 3, 2023

(54) ALGAL CULTIVATION SYSTEM AND A PROCESS FOR BIOMASS PRODUCTION

(71) Applicant: RELIANCE INDUSTRIES LIMITED, Mumbai (IN)

(72) Inventors: Natarajan Mohan, Villupuram District (IN); Amit Vinod Mahulkar, Nagpur (IN); Ganesh K. Veluswamy, Chennai (IN); Avinash Ramchandra Khopkar, Pune (IN); Ganesh Lakshman Maddikeri, Solapur (IN); Nitin Narayan Kirdat, Sangli (IN); Arun Banerjee, Kharghar (IN); Ravikumar Yelchuri, Ongole (IN)

(73) Assignee: RELIANCE INDUSTRIES LIMITED, Maharashtra (IN)

( * ) Notice: Subject to any disclaimer, the term of this patent is extended or adjusted under 35 U.S.C. 154(b) by 478 days.

(21) Appl. No.: 16/607,139

(22) PCT Filed: Apr. 30, 2018

(86) PCT No.: PCT/IB2018/052980
§ 371 (c)(1),
(2) Date: Oct. 22, 2019

(87) PCT Pub. No.: WO2018/203211
PCT Pub. Date: Nov. 8, 2018

(65) Prior Publication Data
US 2020/0385662 A1    Dec. 10, 2020

(30) Foreign Application Priority Data
May 2, 2017    (IN) .............................. 201621037647

(51) Int. Cl.
*C12M 1/00*    (2006.01)
*C12N 1/12*    (2006.01)

(52) U.S. Cl.
CPC ............ *C12M 23/18* (2013.01); *C12M 21/02* (2013.01); *C12M 23/38* (2013.01); *C12M 23/58* (2013.01);
(Continued)

(58) Field of Classification Search
None
See application file for complete search history.

(56) References Cited

U.S. PATENT DOCUMENTS 4,005,546 A * 2/1977 Oswald ..................... C02F 3/32
                                                    435/946
4,439,315 A * 3/1984 Whiteside .............. C12M 23/36
                                                    210/120

(Continued)

FOREIGN PATENT DOCUMENTS

CN        103911274 A  *  7/2014  ............ C12M 21/02
WO    WO-2010012028 A1 *  2/2010  ............ C12M 21/02

OTHER PUBLICATIONS

Bilanovic et al., Co-cultivation of microalgae and nitrifiers for higher biomass production and better carbon capture, Aug. 25, 2016, Bioresource Technology 220, pp. 282-288 (Year: 2016).*

(Continued)

*Primary Examiner* — Holly Kipouros
(74) *Attorney, Agent, or Firm* — GOTTLIEB, RACKMAN & REISMAN, P.C.

(57) ABSTRACT

The present disclosure relates to an algal cultivation system comprising an algal pond. The algal pond comprises a growth chamber containing algal culture which is exposed to light to enable rapid growth of algae therein, and a regeneration chamber which is substantially devoid of light and configured to provide a residence time to algal culture for repair of damaged proteins of algal cells. The present disclosure also relates to a process for biomass production, comprising circulating algal culture using convection cur- (Continued)

rent or forced convection, between the growth chamber and the regeneration chamber. The system and process facilitate in increasing biomass and mitigating salinity and/or temperature variations in the algal culture (A).

11 Claims, 14 Drawing Sheets

(52) U.S. Cl.
CPC ............ *C12M 27/20* (2013.01); *C12M 29/00* (2013.01); *C12N 1/12* (2013.01)

(56) References Cited

U.S. PATENT DOCUMENTS

| | | | |
|---|---|---|---|
| 8,642,326 B1* | 2/2014 | Schaefer | ................ C12M 21/02 435/257.1 |
| 2013/0095544 A1* | 4/2013 | Berlowitz | ............. C12P 7/6463 435/166 |
| 2014/0004600 A1 | 1/2014 | Tarassov et al. | |
| 2014/0042085 A1* | 2/2014 | Blanc | ...................... C02F 3/341 210/150 |
| 2015/0322393 A1 | 11/2015 | Meiser et al. | |
| 2015/0344830 A1* | 12/2015 | Ganuza | .................. C12M 21/02 435/292.1 |

OTHER PUBLICATIONS

Gibson, Growth rate, maintenance energy and pigmentation of planktonic Cyanophyta during one-hour light: dark cycles, 1985, Br. phycol. J., 20:155-161 (Year: 1985).*

ISA/IN, PCT International Search Report and Written Opinion dated Aug. 1, 2018 issued in PCT International Application No. PCT/IB2018/052980 filed Apr. 30, 2018.

* cited by examiner

ALGAL CULTIVATION SYSTEM AND A PROCESS FOR BIOMASS PRODUCTION

CROSS-REFERENCE TO RELATED APPLICATIONS

This application is the United States National Stage entry under 35 U.S.C. 371 of PCT/IB2018/052980, filed on Apr. 30, 2018, which in turn claims the priority of Indian Patent Application No. 201621037647, filed May 2, 2017, the contents of each of which are hereby incorporated by reference in their entirety.

FIELD

The present disclosure relates to an algal cultivation system and a process for biomass production.

DEFINITION

As used in the present disclosure, the following term is generally intended to have the meaning as set forth below, except to the extent that the context in which they are used indicate otherwise.

Salinity Sensor refers to a sensor which determines the salinity of algal culture.

BACKGROUND

Photosynthetic biological organisms such as algae thrive on efficient light utilization, for example, in presence of sunlight, for faster growth or multiplication. Conventionally, algae are grown in large open channels or tanks at depths of 15-30 cm in saline water. Algae are dependent on abundant light availability for a better photo-synthetic performance or growth. The cultivation of algae at higher concentrations above 1 g/l is limited by the availability of light, since the light gets attenuated very fast, at relative depths such as 15-30 cm. In order to achieve and operate at higher concentrations, it is necessary to carry out the cultivation of algae at shallow depths, i.e., below 10 cm, to decrease the light attenuation losses, and to reduce the cost associated with handling of water. Typically, the evaporation rate is constant irrespective of the culture being deep or shallow (below 10 cm); however, the damage (due to evaporation) is more felt when the depth of tanks or open channels is below 10 cm. This is because the salinity increases rapidly in shallow ponds as compared to deep ponds.

Volumetric productivity of the photosynthetic biological organisms is defined as the product of operating concentration of the organisms and specific growth rate of the organisms. The specific growth rate is determined by the light utilization, which directly affects the overall volumetric productivity. Hence, efficient utilization of the light is the key to achieve a higher volumetric productivity. Shallow pond concept provides a great advantage by decreasing the optical path and increasing the light utilization efficiency. However, in shallow depth systems, evaporation is a critical problem that affects the operation of the shallow depth systems. Evaporation leads to rapid change in salinity of the operating volume and temperature, which in turn leads to biological stress in the photosynthetic organisms. Eventually, the culture growth rate is disturbed or affected, leading to a lower volumetric productivity.

Moreover, algae are exposed to light during daytime which in turn generates biomass. Upon continuous exposure to light, it damages the proteins associated with the photosynthetic machinery. This in turn reduces the rate of photosynthesis over time, thereby resulting in lower algal productivity.

There is, therefore, felt a need for a system and a process that obviate the above mentioned drawbacks.

OBJECTS

Some of the objects of the present disclosure, which at least one embodiment herein satisfies, are as follows:

An object of the present disclosure is to provide a system for cultivating algae at shallow depths.

Another object of the present disclosure is to provide a system for cultivating algae at shallow depths without affecting the salinity and the temperature of fluid containing algal culture.

Yet another object of the present disclosure is to provide a system that enhances algal productivity.

Still another object of the present disclosure is to provide a system that reduces temperature and salinity variations in raceway ponds or algal ponds during daytime.

Yet another object of the present disclosure is to provide a process that facilitates biomass production.

Other objects and advantages of the present disclosure will be more apparent from the following description, which is not intended to limit the scope of the present disclosure.

SUMMARY

The present disclosure relates to an algal cultivation system comprising an algal pond. The algal pond comprises a growth chamber containing algal culture and a regeneration chamber.

The growth chamber is exposed to light to enable rapid growth of algae contained therein. The regeneration chamber is substantially devoid of light, wherein the regeneration chamber is configured to provide a controlled residence time to algal culture for repair of damaged proteins of algal cells.

The growth chamber and the regeneration chamber are in controlled fluid communication with each other.

In one embodiment of the present disclosure, the system further comprises at least one pumping device and at least one sensor selected from the group consisting of level sensors, salinity sensor and temperature sensor. The pumping device is configured to facilitate the transfer of fluid containing the algal culture between the growth chamber and the regeneration chamber. The pumping device is one of a paddle wheel and a pump.

In another embodiment of the present disclosure, the system further comprises at least two level sensors, wherein each of the sensors is disposed in the growth chamber and the regeneration chamber. The level sensors are configured to generate level signals corresponding to the levels in the respective chambers.

In yet another embodiment of the present disclosure, the system further comprises a salinity sensor disposed in the growth chamber.

In still another embodiment of the present disclosure, the system further comprises a temperature sensor disposed in the growth chamber.

In yet another embodiment of the present disclosure, the system further comprises a controller. The controller co-operates with the pumping device, the level sensors, the salinity sensor and the temperature sensor. The controller is configured to receive level signals from the level sensors, salinity signals from the salinity sensor and temperature signals from the temperature sensor. The controller is further configured to generate an output signal to trigger and stop the pumping device.

The output signal is fed to the pumping device to regulate the flow of fluid containing the algal culture between the growth chamber and the regeneration chamber to maintain a desired level of fluid in each of the chambers.

The system further comprises at least two valves configured to control the flow of fluid containing the algal culture between the growth chamber and the regeneration chamber.

The depth of the growth chamber is less than 10 cm. A plurality of baffles is vertically disposed in the regeneration chamber.

The system further comprises a dividing-element. The dividing-element is disposed in the algal pond to divide the algal pond into the growth chamber and the regeneration chamber to create a ballast between the growth chamber and the regeneration chamber to mitigate salinity and/or temperature variations in the algal culture.

The regeneration chamber is disposed operatively below the growth chamber such that the regeneration chamber is substantially devoid of light.

The system further comprises a cover. The cover is disposed on the regeneration chamber such that the regeneration chamber is substantially devoid of light. An inlet is configured on the cover to facilitate the introduction of fluid containing the algal culture, nutrients and inoculum into the regeneration chamber.

In an embodiment, the algal pond is configured to function as the growth chamber on being exposed to light and configured to function as the regeneration chamber on being substantially devoid of light.

Typically, the source of the light is sunlight or LED light.

The present disclosure also relates a process for biomass production. The process comprises circulating algal culture using convection current or forced convection in a controlled manner, between a growth chamber (206a, 10) wherein the algal culture is exposed to light and a regeneration chamber (206b, 12) wherein the algal culture is exposed to darkness for the growth and regeneration of the algal culture respectively for biomass production.

The ratio of the time duration in the growth chamber to the time duration in the regeneration chamber is in the range of 2 to 4.

The salinity and/or temperature are varied by transferring fluid containing the algal culture (A) between the growth chamber and the regeneration chamber.

BRIEF DESCRIPTION OF ACCOMPANYING DRAWING

An algal cultivation system will now be described with the help of the accompanying drawing, in which.

Figure 1:
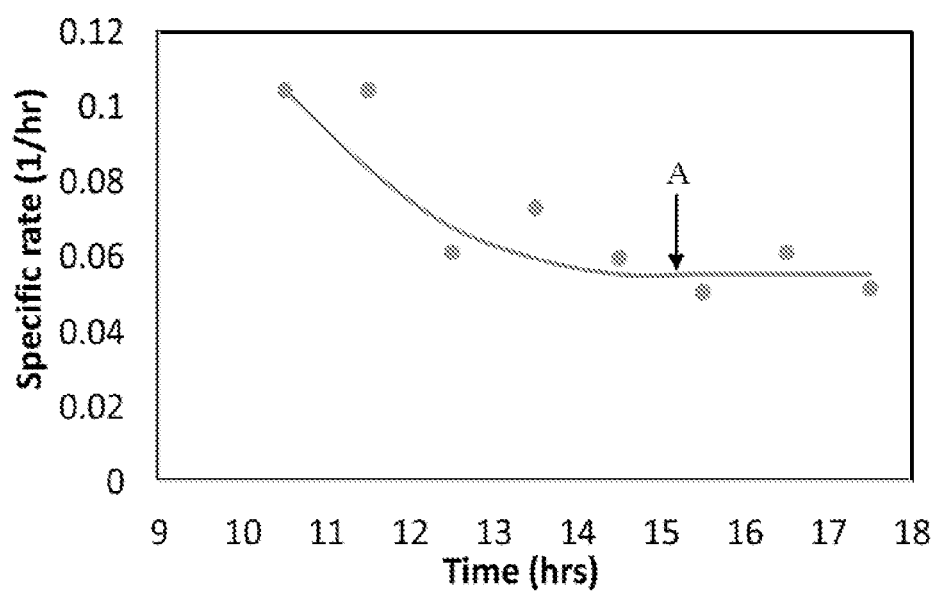
FIG. 1 depicts a graph of the variation in specific rate (rate of photosynthesis) of algal culture with time in a conventional open system.

TABLE 1 provides a list of the reference numerals used:

| COMPONENTS | REFERENCE NUMERALS |
|---|---|
| Algal cultivation system | (200, 300) |
| Algal pond | (202, 16) |
| Dividing-element | (204) |
| Growth chamber | (206a, 10) |
| Regeneration chamber | (206b, 12) |
| Pumping device | (208) |
| Cover | (210) |
| Inlet | (211) |
| Two level sensors | (212a, 212b) |
| Salinity sensor | (214) |
| Temperature sensor | (216) |
| Controller | (218) |
| Valves | (207a, 207b) |
| Plurality of baffles | (14) |
| Depth | (d) |

DETAILED DESCRIPTION

The demand of alternative and renewable biological sources of fuels has increased in the recent years because of the increased shortage of fossil fuels and the rising environmental pollution. Biofuels produced by living organisms such as algae are alternative fuels to those derived from crude oil. Algae are the preferred choice for producing many value added products such as biofuels, as they are able to efficiently convert sunlight and carbon dioxide to biomass which in turn may be converted to value added products.

Typically, photosynthetic algae (photosynthetic machinery) are grown in open ponds or in closed systems such as photo-bioreactors. One advantage of an open pond is cost, as an open pond can be constructed easily and is relatively inexpensive to operate. However, open ponds are subjected to the weather (e.g., temperature and rainfall) and other conditions of the environment surrounding the pond.

FIG. 1 depicts a graph of the variation in specific rate (rate of photosynthesis) of algal culture with time in a conventional open system.

Figure 2:
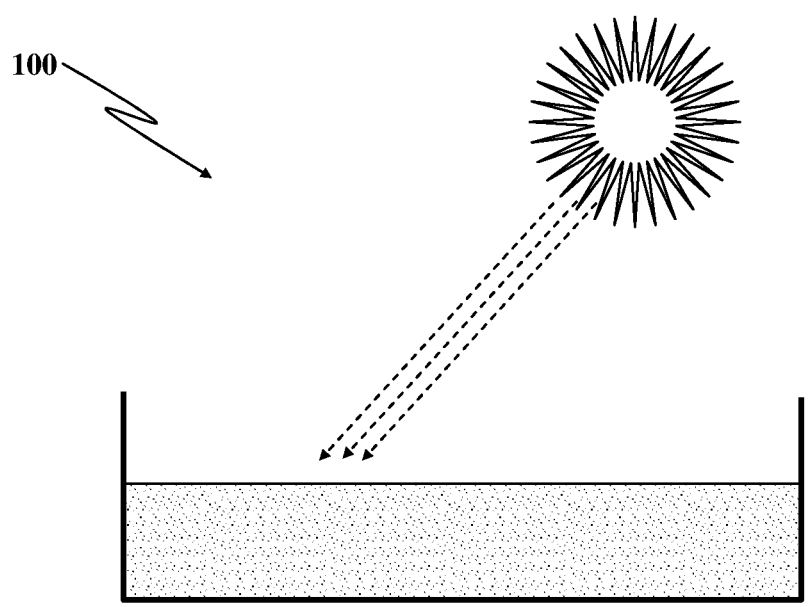
FIG. 2 illustrates a schematic view of a conventional open system for cultivation of algae.

FIG. 2 illustrates a schematic view of a conventional open system (100) for cultivation of algae. The system (100) comprises a pond containing saline water. As described herein above, the conventional open system (100) has one or more drawbacks such as rapid variations in the operating conditions which results in lower algal productivity. The system (100) offers stable operating conditions when there is no drastic change in the salinity. However, the operating algal culture density or concentration is less. The concentration of algae can be increased only if the operational depth of the pond is decreased. Decreasing the depth of the conventional open system (100) (pond) has its own limitations in the form of rapid or large salinity variations due to atmospheric evaporation, which can lead to biological stress on the photosynthetic performance of the photosynthetic organism.

Moreover, proteins associated with algal photosynthetic machinery are damaged upon continuous exposure to sunlight. Due to this, the photosynthetic rate is reduced, thereby resulting in lower algal productivity as illustrated in FIG. 1.

The present disclosure, therefore, envisages a system and a process that obviate the above mentioned drawbacks.

The algal cultivation system is described with reference to FIGS. 3 and 6A to 6D. The algal cultivation system (200, 300) comprises an algal pond (202, 16), wherein the algal pond (202, 16) comprises at least one growth chamber (206a, 10) containing algal culture (A), and at least one regeneration chamber (206b, 12). In an embodiment, the algal pond (202, 16) is a raceway pond.

The growth chamber (206a, 10) is exposed to light to enable rapid growth of algae contained therein. The regeneration chamber (206b, 12) is substantially devoid of light and configured to provide a controlled residence time to algal culture for repair of damaged proteins of algal cells. The algal culture (A) with repaired proteins is circulated to the growth chamber (206a, 10).

The growth chamber (206a, 10) and the regeneration chamber (206b, 12) are in controlled fluid communication with each other to mitigate salinity and/or temperature variations in the algal culture (A) by transfer of fluid containing the algal culture (A) between the growth chamber (206a, 10) and the regeneration chamber (206b, 12).

Figure 11A:
FIG. 11A illustrates an experimental setup of control pond and experimental pond (covered with black cloth)

In another embodiment as shown in FIG. 11A, the algal pond is configured to function as the growth chamber (206a, 10) on being exposed to light and configured to function as the regeneration chamber (206b, 12) on being substantially devoid of light.

In an embodiment, the source of the light is sunlight. In another embodiment, the source of the light is LED light.

Figure 3:
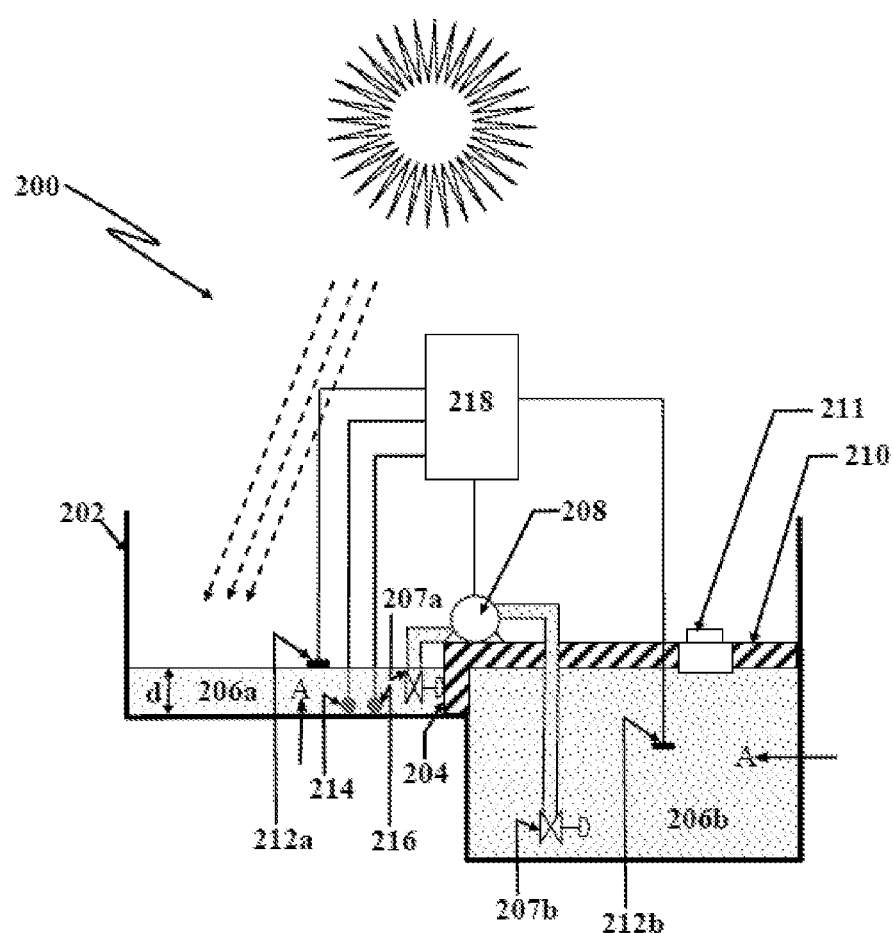
FIG. 3 illustrates a schematic view of a system for cultivation of algae in accordance with one embodiment of the present disclosure.

In accordance with one embodiment of the present disclosure and with reference to FIG. 3, a dividing-element (204) is disposed in the algal pond (202) to divide the algal pond (202) into the growth chamber (206a) and the regeneration chamber (206b), thereby creating a ballast or buffer between the growth chamber (206a) and the regeneration chamber (206b) to mitigate salinity and/or temperature variations in the algal culture (A). The volume of fluid (containing the algal culture (A)) contained in the growth chamber (206a) is exposed to light, and the volume of the fluid in the regeneration chamber (206b) is substantially devoid of light. The growth chamber (206a) has a depth (d) of less than 10 cm (shallow depth).

In accordance with an embodiment of the present disclosure, a cover (210) is disposed on the regeneration chamber (206b) such that the regeneration chamber (206b) is substantially devoid of light. An inlet (211) is configured on the cover (210) to facilitate the introduction of fluid containing the algal culture (A), nutrients and inoculum into the regeneration chamber (206b).

The system (200) further comprises at least one pumping device (208) and at least one sensor selected from the group consisting of level sensor (212a, 212b), salinity sensor (214) and temperature sensor (216). The pumping device (208) is configured to facilitate the transfer of fluid containing the algal culture (A) between the growth chamber (206a) and the regeneration chamber (206b). In accordance with one embodiment of the present disclosure, the pumping device (208) is one of a paddle wheel and a pump.

At least two valves (207a, 207b) are fitted in the pond (202). The valves are configured to control the flow of fluid containing the algal culture (A) between the growth chamber (206a) and the regeneration chamber (206b). The valve (207a) is also configured to prevent the back flow of the fluid from the growth chamber (206a) to the regeneration chamber (206b).

The system (200) further comprises at least two level sensors (212a, 212b). Each of the sensors (212a, 212b) is disposed in the growth chamber (206a) and the regeneration chamber (206b). The level sensors (212a, 212b) are configured to generate signals corresponding to the levels in the respective chambers.

The system (200) further comprises a salinity sensor (214), wherein the salinity sensor (214) is disposed in the growth chamber (206a).

The system (200) further comprises a temperature sensor (216). The temperature sensor (216) is disposed in the growth chamber (206a).

The system (200) further comprises a controller (218). The controller (218) co-operates with the pumping device (208), the level sensors (212a, 212b), the salinity sensor (214) and the temperature sensor (216). The controller (218) is configured to receive the level signals from the level sensors (212a, 212b), the salinity signals from the salinity sensor (214) and the temperature signals, from the temperature sensor (216). The controller (218) is further configured to generate an output signal based on the level signals, the salinity signals and the temperature signals to trigger and stop the pumping device (208).

The output signal from the controller (218) is fed to the pumping device (208) to regulate the flow of the fluid between the growth chamber (206a) and the regeneration chamber (206b) to maintain a desired level of the fluid in each of the chambers (206a and 206b). Due to this, the effect of evaporation in the growth chamber (206a) can be attenuated which in turn facilitates in controlling the salinity and temperature variations of the algal culture (A) in the growth chamber (206a).

In accordance with another embodiment of the present disclosure, an algal cultivation system (300) is envisaged as shown in FIGS. 6A to 6D. The regeneration chamber (12), in case of the algal cultivation system (300), is disposed operatively below the growth chamber (10) such that the regeneration chamber (12) is substantially devoid of light.

In the growth chamber (10), the algal culture (A) is continuously exposed to sunlight, i.e., high light intensity conditions. Due to this, antenna proteins of algae are damaged, thereby affecting the algal productivity. It is therefore necessary to heal the damaged proteins so as to improve the algal productivity. The volume of the growth chamber (10) or light zone is determined by the formula provided herein below.

Light zone volume ($V_L$)=Footprint area (area occupied by the system (100)($A$)*Depth ($D$) of the light zone The damaged proteins are healed by providing intermittent regeneration time for the algal cells. Particularly, the algal culture/cells are moved from the growth chamber (10) to the regeneration chamber (sump) (12) which is a low light or dark regeneration chamber. The arrows indicate the direction of movement of the algal culture between the growth chamber (10) and the regeneration chamber (sump) (12). The residence time or regeneration time of the algal culture in the sump (12) is adjusted such that it is sufficient for the healing or repairing of the damaged proteins. The residence time of the algal culture in the sump (12) should be greater than 30 minutes and less than 90 minutes. The residence time of the algal culture in the sump (12) should be less than 90 minutes to obviate initiating respiration related biomass losses. In accordance with the present disclosure, a plurality of baffles (14) are vertically disposed in the regeneration chamber (12) to facilitate the movement of the algal culture (A) through the regeneration chamber (12). The volume of the regeneration chamber (12) is determined by the formula provided herein below.

Regeneration volume ($V_R$)=volume ($V_L$) of the growth chamber/time ratio ($R$)

Once the proteins are healed or repaired, the algal culture is moved back or introduced into the growth chamber (10) for further biomass generation. In accordance with the present disclosure, when the algal culture with repaired proteins exits the sump (12), the algal culture with damaged proteins enters the sump (12) from the growth chamber (10). The velocity of the algal culture in the system (300) is in the range of 5 cm/s to 10 cm/s so as to avoid settling of algal cells. The flow-rate (Q) of the algal culture (A) in the system (300) is calculated by the formula provided herein below.

Flow rate of culture ($Q$)=Regeneration volume ($V_R$)/Time in regeneration zone ($T_R$)

In another aspect of the present disclosure, a process for biomass production in the algal pond (202, 16) is envisaged. The process comprises circulating algal culture using convection current or forced convection in a controlled manner, between a growth chamber (206a, 10) wherein the algal culture is exposed to light and a regeneration chamber (206b, 12) wherein the algal culture is exposed to darkness for the growth and regeneration of the algal culture respectively for biomass production The ratio of the time duration in the growth chamber (206a, 10) to the time duration in the regeneration chamber (206b, 12) is in the range of 2 to 4.

The salinity and/or temperature are varied by transferring fluid containing the algal culture (A) between the growth chamber (206a, 10) and the regeneration chamber (206b, 12).

The algal culture (A) from the regeneration chamber (206b, 12) is circulated to the growth chamber (206a, 10) using convection current or forced convection.

Due to the alternating light and dark cycle, the biomass production is increased by at least 20% as compared to that of conventional systems and processes.

The system and process of the present disclosure facilitate in repairing/healing damaged algal cells, thereby increasing the biomass productivity.

During rainfall, since the growth chamber (206a) is exposed to atmosphere and the depth of the growth chamber (206a) is less than 10 cm, there is an increase in the level of the fluid in the growth chamber (206a). This results in dilution of the concentration of the algal culture (A) contained therein. In order to maintain a desired concentration of the algal culture (A) in the growth chamber (206a), there is a need to stop the transfer of the fluid between the growth chamber (206a) and the regeneration chamber (206b). The transfer of the fluid to and from the chambers (206a and 206b) is stopped with the help of the valves (207a, 207b).

After it stops raining, the circulation of the fluid between the two chambers (206a, 206b) is resumed with the help of the valves (207a, 207b), and the optimum conditions such as level of the fluid, temperature of the fluid, concentration of the algal culture (A), and salinity of the algal culture (A) in the growth chamber (206a) are attained. This is further illustrated with respect to FIG. 4.

Figure 4:
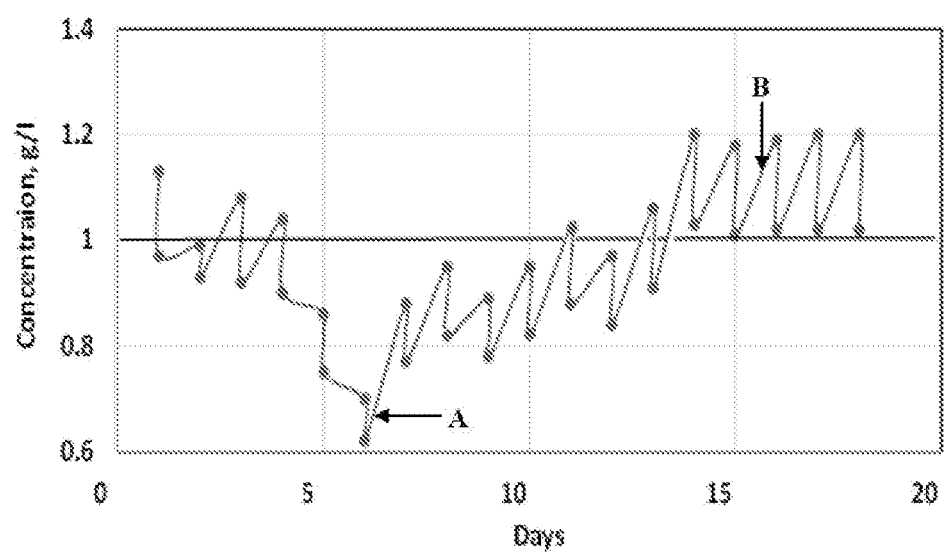
FIG. 4 depicts a graph of the variation in concentration of algal culture with time when the system of the present disclosure is used for cultivation of algae.

FIG. 4 depicts a graph of the variation in concentration of algal culture with time when the system of the present disclosure is used for cultivation of algae. During rainfall, the algal culture (A) from the growth chamber (206a) is pumped into the regeneration chamber (206b) with the help of the valve (207a). In accordance with an embodiment of the present disclosure, the valve (207a) is a non-return valve (NRV). After is stops raining, the system (200) is back on continuous circulation mode. It is observed that due to continuous rain during day 3 to day 15, the algal culture from the compartment (206a) is pumped into the compartment (206b), via the non-return valve (NRV).

Moreover, since the regeneration chamber (206b) received no sunlight, the rate of photosynthesis decreased, thereby resulting in a dip in the concentration of the algal culture (A) (represented by A—as shown in FIG. 4). Due to rainfall, the valves (207a and 207b) are closed, and the pumping device (208) is also stopped after the algal culture (A) from the growth chamber (206a) is pumped into the regeneration chamber (206b).

After it stops raining, the circulation of the fluid between the two chambers (206a, 206b) is resumed with the help of the valves (207a, 207b), and the optimum conditions such as level of the fluid, temperature of the fluid, concentration of the algal culture (A), and salinity of the algal culture (A) in the growth chamber (206a) are attained. This is observed from day 15 to day 19 (represented by curve B—as shown in FIG. 4), as there was an increase in the algal concentration when the desired levels of salinity, temperature, concentration of the algal culture (A) and the level of the fluid in the growth chamber (206a) were attained.

The system (200) operates at shallower depths, i.e., less than 10 cm. This ensures maximum utilization of sunlight with minimum attenuation losses. This is further illustrated with respect to FIG. 5.

Figure 5:
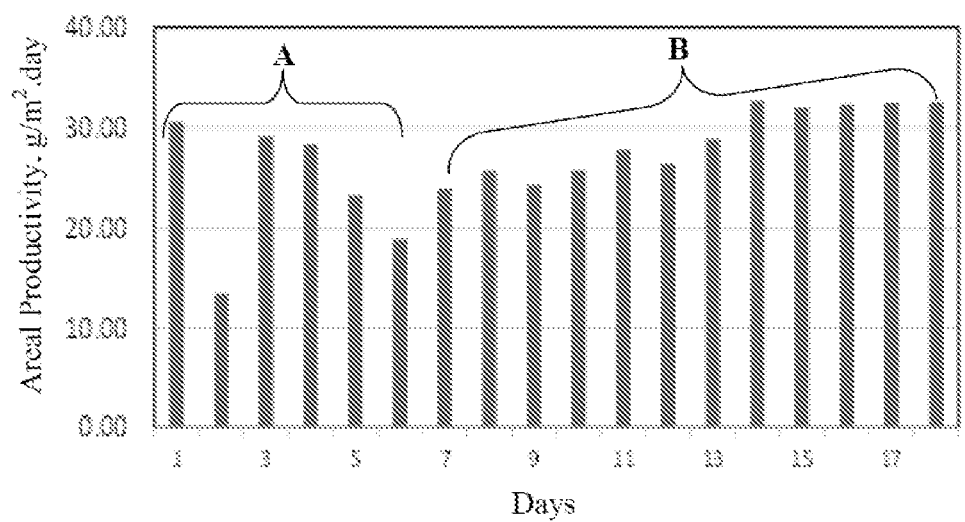
FIG. 5 illustrates a graph of productivity of algae versus time when the system of the present disclosure is used for cultivation of algae.
Figure 6A:
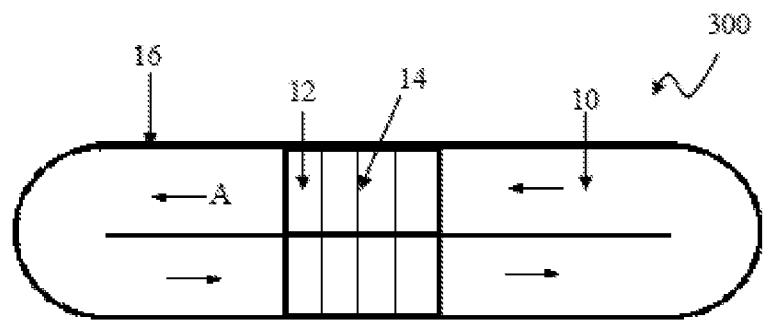
FIGS. 6A to 6D illustrates a schematic view of a system for cultivation of algae in accordance with another embodiment of the present disclosure.
Figure 6B:
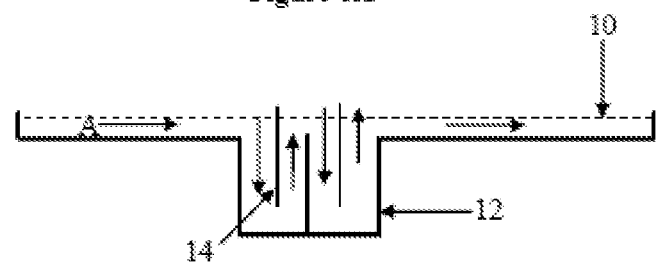
Figure 6C:
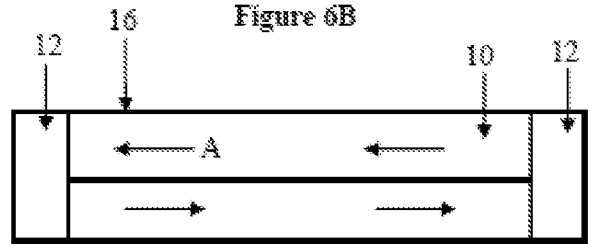
Figure 6D:
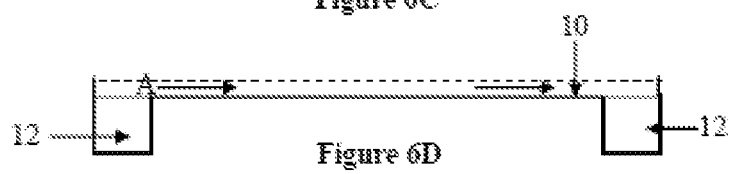

FIG. 5 illustrates a graph of productivity of algae versus time when the system of the present disclosure is used for cultivation of algae. During rainfall, the algal culture (A) from the growth chamber (206a) is pumped into the regeneration chamber (206b) with the help of the non-return valve (NRV). It is observed that due to continuous rainfall during day 2 to day 6 respectively, the regeneration chamber (206b) received no sunlight, the rate of photosynthesis decreases, thereby resulting in a dip in the concentration of the algal culture (A) (represented by A—as shown in FIG. 5).

After it stops raining, the circulation of the fluid between the two chambers (206a and 206b) is resumed and the optimum conditions such as level of the fluid, temperature of the algal culture (A), concentration of the algal culture (A), and salinity of the algal culture (A)) in the growth chamber (206a) are attained. This is observed from day 7 to day 17 (represented by B—as shown in FIG. 5), as there was an increase in the algal concentration when the desired levels of the salinity, temperature, concentration of the algal culture (A) and the level of the fluid were attained in the growth chamber (206a).

The system (200) is capable of growing and maintaining photosynthetic biological micro-organisms (such as algae) at higher volumetric concentrations, typically above 1 g/l, and at depths (operational depths) lesser than 10 cm.

Figure 7:
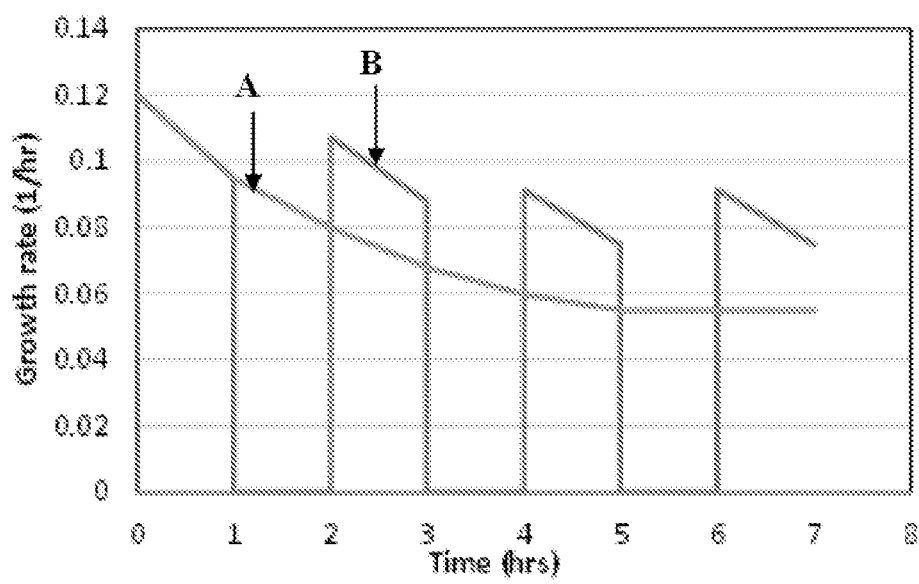
FIG. 7 depicts a graph of the variation in growth rate of algal culture in accordance with the present disclosure.

FIG. 7 depicts a graph of the variation in growth rate of algal culture in accordance with the present disclosure. Particularly, FIG. 7 depicts a comparison of specific rate (growth rate) of the algal culture which is exposed continuously to sunlight (represented by A) as compared to the algal culture exposed to the sunlight for 1 hour, followed by 1 hour of residence time (represented by B) of the algal culture in the sump (12). From FIG. 7, it is found that the algal culture grown in accordance with the present disclosure is increased as compared to that of the algal culture which is exposed continuously to sunlight. In accordance with the present disclosure, due to the recovery of algal proteins, the biomass productivity is increased by at least 20% as compared to that obtained when the algal culture is exposed continuously to the sunlight.

The travel time of the algal culture from one regeneration chamber (12) to the other regeneration chamber is light time. The ratio of the light time to the regeneration time is time ratio (R).

The time ratio (R) is determined by the formula provided herein below.

Ratio $(R)$ = Time in growth chamber or light zone $(T_L)$/Time in sump or regeneration chamber $(T_R)$ The time ratio (R) is in the range of 2 to 4. The time required for regenerating the damaged algal cells is in the range of 15 mins to 60 mins. In an embodiment, the process includes the step of allowing the algal culture (A) to reside in the growth chamber (206a, 10) for a time which is twice to that of the regeneration chamber (206b, 12).

Figure 8:
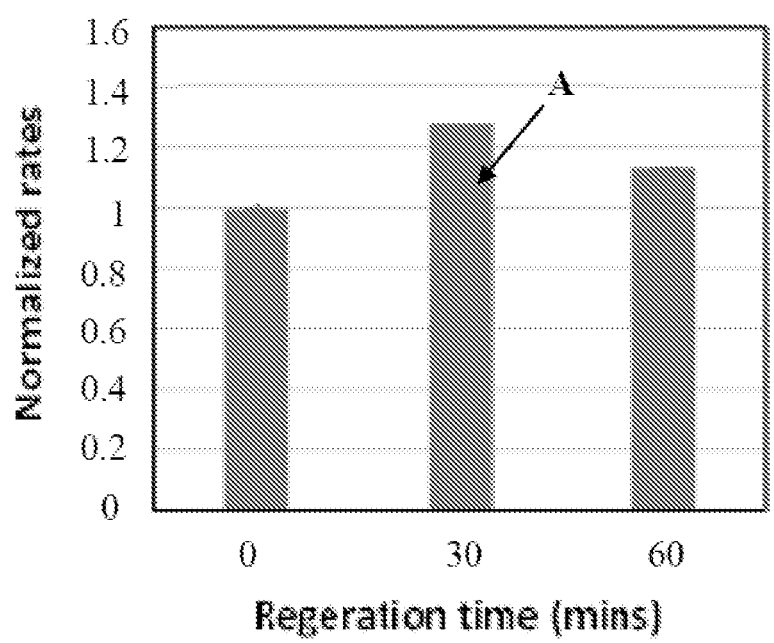
FIG. 8 illustrates a graph of normalized growth of algae versus regeneration time of algae in accordance with the present disclosure.

FIG. 8 illustrates a graph of normalized growth of algae versus regeneration time of algae in accordance with the present disclosure. In accordance with one embodiment of the present disclosure, the optimum time required for regenerating the damaged algal cells is 30 mins (represented by curve A—as shown in FIG. 8).

The present disclosure is further described in light of the following experiments which are set forth for illustration purpose only and not to be construed for limiting the scope of the disclosure. The following experiments can be scaled up to industrial/commercial scale and the results obtained can be extrapolated to industrial scale.

Experiment 1

For the purpose of simulation experiments, a single experimental tank with dimensions 30 cm×30 cm×7 cm was used. An algal culture (Nannochloris obtained from Morva, Bhayander, Maharashtra) was grown in the experimental tank. The experimental tank was placed below an LED bank comprising of cool white LEDs. The experimental tank functioned as a growth chamber on exposure to light when the LED was switched ON and functioned as a regeneration chamber on being substantially devoid of light by switching OFF the LED light. The intensity of the LEDs was adjusted such that the irradiance at the surface of the algal culture was set to a 1000 $\mu E/m^2 \cdot s$. The experimental measurements were replicated for two experimental tanks for replicate measurements. The control measurements were also conducted in two individual control tanks under a separate LED bank with continuous exposure to light. The pH was maintained at 7.0 by sparging $CO_2$ with the help of pH controller.

Experiment 1a—Estimation of Optimum Value of Dark Time

The depth of the culture in the tank was maintained at 3 cm. The LED light was turned ON and OFF using a timer to generate alternate light cycles and dark cycles respectively. Various combinations of light time (time duration of light cycle) and dark time (time duration of dark cycle) were studied at constant light intensity (1000 $\mu E/m2 \cdot s$).

Figure 9:
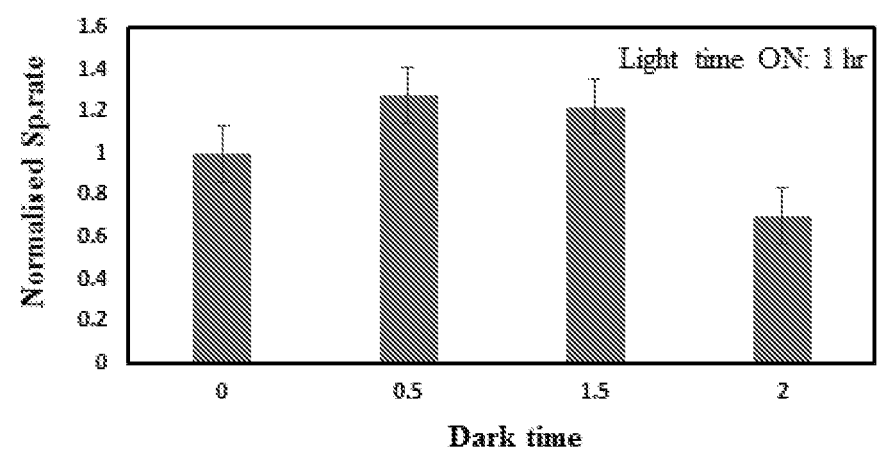
FIG. 9 illustrates a graph of normalized growth rates of algae versus varying values of dark time.

The alternate light cycles and dark cycles were carried out such that the light time (time duration of light cycle) was kept constant (1 hour) while the dark time (time duration of dark cycle) was varied from 30 mins to 120 mins. FIG. 9 illustrates a graph of normalized growth rates of algae versus varying values of dark time.

The experimental results showed maxima for 30 mins of dark time. This shows that dark time lesser than 30 minutes would be insufficient for removal/consumption of the rate inhibiting intermediates or to repair the damaged protein whereas the dark time longer than 30 minutes would result in biomass loss in the dark.

Experiment 1b—Estimation of Optimum Optical Density

Figure 10A:
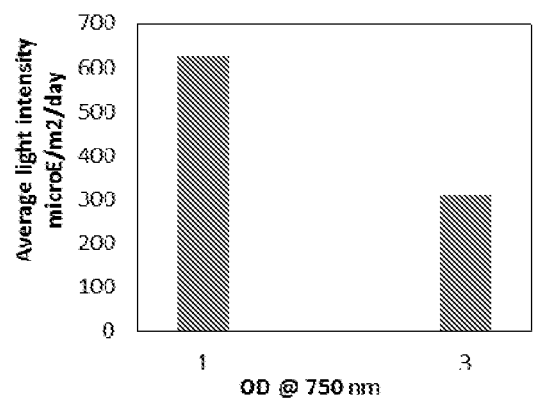
FIG. 10A illustrates a graph of the average light density for algal culture having optical density values as 1 and 3.

The experiments were conducted for different culture densities values of 320 mg/l and 960 mg/l corresponding to optical density (OD) values of 1 and 3 respectively. The intensity of light was 1000 $\mu E/m^2 \cdot s$ and the measurements were done at a wavelength of 750 nm. FIG. 10A illustrates a graph of the average light density for algal culture having optical density values as 1 and 3. It was seen that the average light density was higher for OD=1 than for OD=3.

Figure 10B:
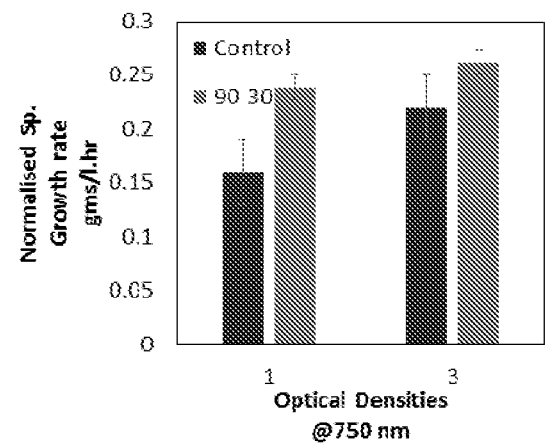
FIG. 10B illustrates a graph of normalized growth rate measured for the experimental tank and the control tank.

The normalized growth rate in the experimental tank was measured for light time of 90 mins and dark time of 30 mins. The normalized growth rate was also measured for the control tank which was exposed to continuous light. FIG. 10B illustrates a graph of normalized growth rate measured for the experimental tank and the control tank.

It was observed that the growth rates in the experimental tank was higher and showed 20% improvement (in both cases) over the growth rates in the control tank even at higher optical density.

Experiment 2—Outdoor Condition Experiment

For the purpose of simulation experiments, an experimental pond setup having a raceway pond having area 1 $m^2$ was used that functioned as a growth chamber when exposed to sunlight and functioned as a regeneration chamber when exposed to darkness by covering with an opaque lid (black cloth). Another raceway pond exposed continuously to sunlight was used as a control pond. An algal culture (*Picochlorum* strain obtained from Karanja, Maharashtra) was grown in the experimental pond and control pond. FIG. 11A shows experimental setup of control pond and experimental pond (covered with black cloth). As per the results obtained from experiment 1a, the light time was maintained at 90 minutes and dark time was maintained for 30 minutes. The pH was maintained by sparging $CO_2$ with the help of pH controller. The light dark cycles were conducted from 9 am in morning to 6 pm in evening. The experimental pond was operated at depth of 10 cm and culture was mixed using four aquarium pumps in each pond. The pond was harvested daily in evening and brought to 2 OD (turbidostat mode).

The areal productivity for control pond was calculated based on increase in OD in 24 hours as $$AP = \frac{\Delta OD \times BDOD \times 100 \; lit}{1 \; m^2} \frac{gm}{m^2} \cdot day$$

In case of experimental pond area productivity is calculated as follows $$AP = \frac{\Delta OD \times BDOD \times 100 \; lit}{1 \; m^2 \times 0.75} \frac{gm}{m^2} \cdot day$$

This areal productivity was normalized with factor 0.75 as the experimental pond received light for only 75% of the time.

Figure 11B:
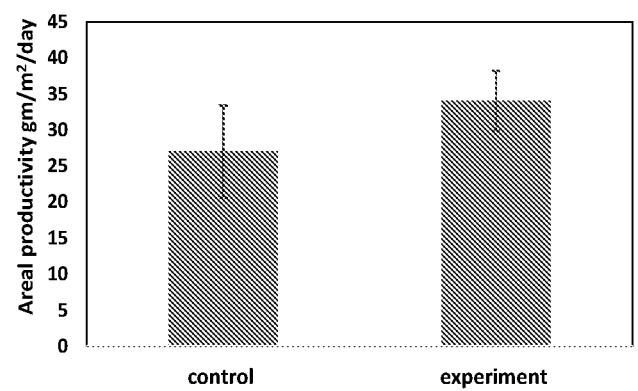
FIG. 11B illustrates a graph of average areal productivity of control pond and experimental pond over 20 days of operation.
Figure 11C:
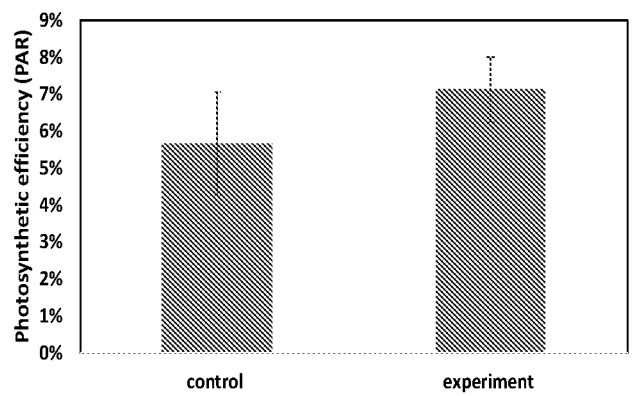
FIG. 11C illustrates a graph of photosynthetic efficiency of control pond and experimental pond over 20 days of operation.

FIG. 11B shows average areal productivity of control pond and experimental pond over 20 days of operation. The average areal productivity for control pond and experimental pond was 27 and 34 gm/m²·day respectively. FIG. 11C shows photosynthetic efficiency of control pond and experimental pond over 20 days of operation. The photosynthetic efficiency on PAR basis is calculated as follows $$PE = \frac{\text{Areal Productivity} \frac{gm}{m^2} \cdot day \times \frac{kJ}{gm}}{\frac{\text{moles of photon}}{day} \times 219 \frac{kJ}{mole}}$$

The incident sunlight data was recorded for 24 hours of operation on each day for calculating the photosynthetic efficiency. The average photosynthetic efficiency for control pond and experimental pond was 5.6% and 7.13% on PAR basis respectively. The experimental pond showed 25% improvement in areal productivity (& photosynthetic efficiency) in comparison to the control pond.

Experiment 3—Effect of Recovery Chamber on the Areal Productivity

Figure 12A:
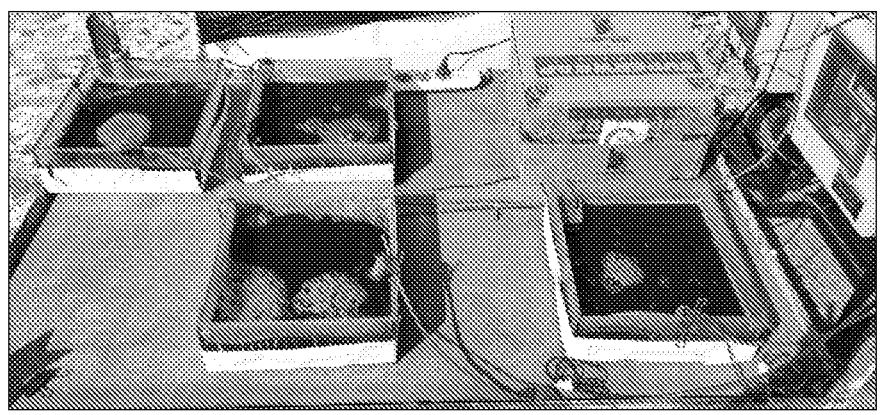
FIG. 12A illustrates an experimental setup which incorporates ability to move the algal culture between the growth chamber and the regeneration chamber.
Figure 12B:
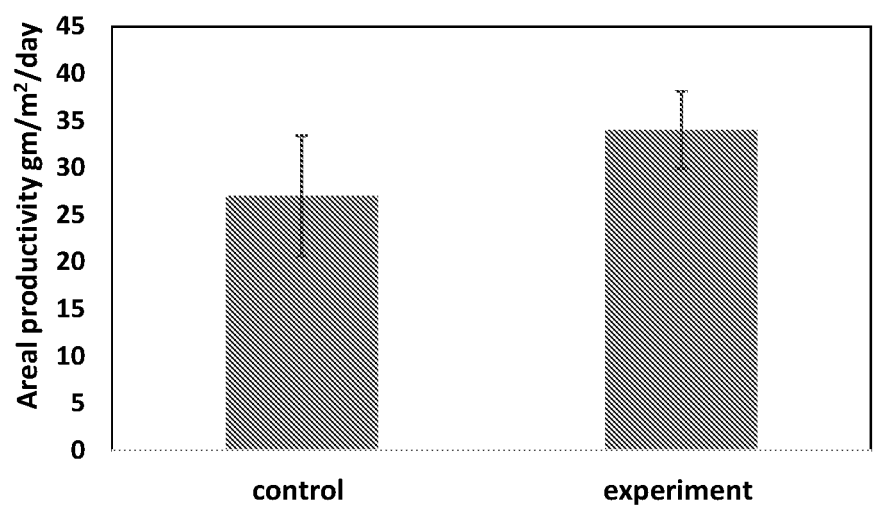
FIG. 12B illustrates a graph of productivity for the experimental and the control tank.

For the purpose of simulation experiments, an experimental setup as shown in FIG. 12A was used for demonstrating the effect of recovery chamber on the areal productivity. Three tanks were used as experimental tank and one was used as a control tank. Each of the three experimental tanks functioned as a growth chamber when exposed to sunlight and functioned as a regeneration chamber when exposed to darkness by covering with an opaque lid (black cloth). FIG. 12A illustrates an experimental setup which incorporates ability to move the algal culture between the growth chamber and the regeneration chamber. In this experiment, the algal culture was moved from one experimental tank to the other after every 30 minutes. At a time, one experimental tank was covered for 30 minutes for simulating the culture flowing through sump. FIG. 12B illustrates a graph of productivity for the experimental and the control tank. The graph depicts an improvement in productivity of the experimental tank over the conventional tank.

TECHNICAL ADVANCES AND ECONOMICAL SIGNIFICANCE

The present disclosure described herein above has several technical advantages including, but not limited to, the realization of a system and a process that:

facilitates algal cultivation at shallower depths, i.e., less than 10 cm, which ensures maximum utilization of light;

does not need additional foot print area as compared to conventional pond or systems;

facilitates in reducing the temperature and salinity variation of the algal culture during the daytime, thereby enhancing the productivity of biomass by at least 20% as compared to that obtained in conventional systems and processes; and does not need additional pumping system to move the algal culture in and out of the regeneration chamber; this is because, the regeneration chamber is disposed operatively below the growth chamber.

The disclosure has been described with reference to the accompanying embodiments which do not limit the scope and ambit of the disclosure. The description provided is purely by way of example and illustration.

The embodiments herein and the various features and advantageous details thereof are explained with reference to the non-limiting embodiments in the following description. Descriptions of well-known components and processing techniques are omitted so as to not unnecessarily obscure the embodiments herein.

The foregoing description of the specific embodiments so fully revealed the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

The use of the expression "at least" or "at least one" suggests the use of one or more elements or ingredients or quantities, as the use may be in the embodiment of the invention to achieve one or more of the desired objects or results.

Any discussion of documents, acts, materials, devices, articles or the like that has been included in this specification is solely for the purpose of providing a context for the invention. It is not to be taken as an admission that any or all of these matters form part of the prior art base or were common general knowledge in the field relevant to the invention as it existed anywhere before the priority date of this application.

In view of the wide variety of embodiments to which the principles of the present invention can be applied, it should be understood that the illustrated embodiments are exemplary only. While considerable emphasis has been placed herein on the particular features of this invention, it will be appreciated that various modifications can be made, and that many changes can be made in the preferred embodiments without departing from the principle of the invention. These and other modifications in the nature of the invention or the preferred embodiments will be apparent to those skilled in the art from the disclosure herein, whereby it is to be distinctly understood that the foregoing descriptive matter is to be interpreted merely as illustrative of the invention and not as a limitation.

The invention claimed is:

1. An algal cultivation system comprising an algal pond, wherein said algal pond comprises:
    a growth chamber containing algal culture, wherein said growth chamber is exposed to light to enable growth of algae contained therein, wherein said growth chamber has a depth (d) of less than 10 cm;
    a regeneration chamber substantially devoid of light, wherein said regeneration chamber is configured to provide a controlled residence time to algal culture for repair of damaged proteins of algal cells;
    a controller co-operating with at least one means for pumping and at least one sensor selected from the group consisting of a plurality of level sensors, a salinity sensor and a temperature sensor,
    wherein said controller is configured to receive level signals from said level sensors, salinity signals from said salinity sensor and temperature signals from said temperature sensor, and wherein said controller is configured to generate an output signal to trigger and stop said means for pumping; and
    a cover (210) disposed on said regeneration chamber (206b) such that the regeneration chamber (206b) is substantially devoid of light,
    wherein said growth chamber and said regeneration chamber are in controlled fluid communication with each other;
    wherein said controlled residence time in said regeneration chamber is in the range of 30 minutes to 90 minutes and said growth chamber is exposed to light for a time period in the range of 60 minutes to 180 minutes;
    wherein a ratio of time duration of said algal culture exposed to light in said growth chamber to said controlled residence time in said regeneration chamber is in the range of 2 to 4;
    wherein said salinity sensor and/or said temperature sensor are disposed in said growth chamber; and
    wherein said output signal is fed to said means for pumping to regulate the flow of fluid containing said algal culture between said growth chamber and said regeneration chamber for maintaining a desired level of fluid in each of said chambers.

2. The system as claimed in claim 1, wherein said means for pumping (208) is one of a paddle wheel and a pump.

3. The system as claimed in claim 1, further comprising at least two level sensors, wherein said level sensors are disposed in said growth chamber and said regeneration chamber, and said level sensors are configured to generate level signals corresponding to the levels in the respective chambers.

4. The system as claimed in claim 1, further comprising at least two valves configured to control the flow of fluid containing the algal culture between said growth chamber and said regeneration chamber.

5. The system as claimed in claim 1, further comprising means for dividing, disposed in said algal pond to divide said algal pond into said growth chamber and said regeneration chamber, thereby creating a ballast between said growth chamber and said regeneration chamber to mitigate salinity and/or temperature variations in the algal culture.

6. The system as claimed in claim 1, wherein said regeneration chamber is disposed operatively below said growth chamber such that the regeneration chamber is substantially devoid of light.

7. The system as claimed in claim 1, further comprising a plurality of baffles vertically disposed in said regeneration chamber.

8. The system as claimed in claim 1, wherein an inlet is configured on said cover to facilitate the introduction of fluid containing said algal culture, nutrients and inoculum into said regeneration chamber.

9. The system as claimed in claim 1, wherein a source of said light is sunlight or LED light.

10. A process for biomass production by using the algal cultivation system as claimed in claim 1 comprising circulating algal culture using convection current or forced convection in a controlled manner, between the growth chamber, wherein the algal culture is exposed to light for a time period in the range of 60 minutes to 180 minutes and the regeneration chamber, wherein the algal culture is exposed to darkness for a time period in the range of 30 minutes to 90 minutes for the growth and regeneration of the algal culture respectively for biomass production; and wherein a ratio of time duration of said algal culture exposed to light in said growth chamber to said controlled residence time in said regeneration chamber is in the range of 2 to 4.

11. The process as claimed in claim 10, wherein salinity and/or temperature are varied by transferring fluid containing the algal culture between the growth chamber and the regeneration chamber.

* * * * *